United States Patent [19]

Sekiyama et al.

[11] Patent Number: 5,334,373

[45] Date of Patent: Aug. 2, 1994

[54] ALLYL ISOTHIOCYANATE SPRAYS

[75] Inventors: Yasushi Sekiyama; Yuichi Mizukami, both of Hyogo; Tessei Yamamoto, Tokyo, all of Japan

[73] Assignees: Nippon Sanso Corporation, Tokyo; The Green Cross Corporation, Osaka, both of Japan

[21] Appl. No.: 913,793

[22] Filed: Jul. 16, 1993

[30] Foreign Application Priority Data

Jul. 18, 1991 [JP] Japan ................................ 3-178370

[51] Int. Cl.$^5$ ...................... A01N 25/06; A01N 47/46
[52] U.S. Cl. .................................. 424/40; 424/195.1; 514/514
[58] Field of Search ................. 424/40, 195.1; 514/514

[56] References Cited

U.S. PATENT DOCUMENTS 3,755,064  8/1973  Maierson ............................. 428/338

FOREIGN PATENT DOCUMENTS

0427862A1  5/1991  European Pat. Off. .

Primary Examiner—John W. Rollins
Attorney, Agent, or Firm—Armstrong, Westerman, Hattori, McLeland & Naughton

[57] ABSTRACT

An allyl isothiocyanate spray prepared by dissolving 0.1 to 10% by weight of an allyl isothiocyanate in liquefied carbon dioxide gas and charging the resulting solution into a pressure vessel under a pressurization so that the liquefied carbon dioxide gas can maintain liquid phase. The spray can practically be employed with safety for bacteriostatic or germicidal treatment or for quality preservation.

4 Claims, 1 Drawing Sheet

ALLYL ISOTHIOCYANATE SPRAYS

BACKGROUND OF THE INVENTION AND STATEMENT OF RELATED ART

This invention relates to allyl isothiocyanate sprays.

Allyl isothiocyanate is also referred to as allyl mustard oil and generally obtained by extraction from a raw material such as mustard and Japanese horseradish (Wasabia japonica Matusum) by steam distillation or by subjecting sodium thiocyanate and allyl chloride to distillation.

The thus obtained allyl mustard oil is primarily utilized as a flavoring agent for foods or as a raw material of pharmaceutical preparations.

The present inventors, having noted the properties of allyl mustard oil and use thereof for bacteriostatic or germicidal treatment or quality preservation, made extensive studies.

They found that satisfactory effect can be exhibited if the allyl mustard oil is used even in a very small amount for the purpose of bacteriostatic or germicidal treatment, etc.

However, allyl mustard oil is an oily liquid which develops peculiar irritating odor and has a comparatively low flash point, so that it involves a number of problems so as to be utilized widely. For example, when allyl mustard oil is used for bacteriostatic or germicidal treatment, it must be vaporized, requiring a vaporizing apparatus for that purpose. Besides, the vaporizing apparatus must indispensably be equipped with a safety device since a low-flash point oil is vaporized, so that the vaporizing apparatus will inevitably be enlarged and expensive. Accordingly, the vaporizing apparatus cannot conveniently be utilized for other purposes than treating a great amount of materials to be treated.

Spraying can be given as an expedient means of vaporizing allyl mustard oil. However, since ordinary spraying methods employ LPG (liquefied petroleum gas) or Freon gas as an atomizing medium, they involve problems in the properties of such gas and in safety. When allyl mustard oil is sprayed using such gaseous medium, the aerosol thus formed comes to have a comparatively great particle size as big as that of mist to stain clothes or fabrics and besides it cannot be sprayed uniformly over a wide area. Accordingly, LPG and Freon cannot be employed for spraying allyl mustard oil due to many inconveniences described above.

There is proposed another technique of spraying a solution of a principal spray agent dissolved in liquefied carbon dioxide gas. This technique can give a very fine aerosol, but solubility of allyl mustard oil in liquefied carbon dioxide gas is not known and further this method involves too many technical problems which must be solved, such as strong irritating odor, correlation between the gaseous composition and the practical bacteriostatic or germicidal effect of the aerosol, etc., to be proposed as a practical method.

OBJECT AND SUMMARY OF THE INVENTION

This invention is directed to provide an allyl isothiocyanate spray having overcome the above problems which is suitably used for bacteriostatic or germicidal treatment. More particularly, this invention is directed to provide a spray, prepared by dissolving allyl isothiocyanate in a high-pressure liquefied carbon dioxide gas which is liquid and charging the resulting solution in liquid form in a pressure vessel, for example a cylinder or a storage tank, etc.

A first aspect of this invention relates to an allyl isothiocyanate spray, comprising a solution of 0.1 to 10% by weight of an allyl isothiocyanate dissolved in liquefied carbon dioxide gas, charged in a pressure vessel with a pressurization so that the liquefied gas can maintain liquid phase.

A second aspect of this invention relates to an allyl isothiocyanate spray comprising a solution of allyl isothiocyanate dissolved in a liquefied carbon dioxide gas, which is prepared by charging 0.1 to 10% by weight of allyl isothiocyanate and then 99.9 to 90% by weight of liquefied carbon dioxide gas to a pressure vessel so as to mix these two components and provide a solution.

A third aspect of this invention relates to an allyl isothiocyanate spray in which said pressure vessel is equipped with an atomizing means and the liquefied carbon dioxide gas serves as a propellant.

A fourth aspect of this invention relates to any of the above allyl isothiocyanate sprays, in which the allyl isothiocyanate is an extract from Japanese horseradish or mustard or a prepurified product thereof.

In the spray according to this invention, the principal spray agent allyl isothiocyanate is dissolved homogeneously in liquefied carbon dioxide gas. Meanwhile, since the liquefied carbon dioxide gas is charged with pressurization into a pressure vessel, the spray, when jetted, is allowed to expand quickly by the release from the high-pressure liquefied carbon dioxide gas, so that the allyl isothiocyanate contained in the spray forms a very fine aerosol. The thus finely divided allyl isothiocyanate stays floating in air over a wide area for an extended time. Accordingly, for example, if a material to be treated is contained in a closed vessel, a gaseous atmosphere of homogeneous composition can be produced to allow the material to be treated to be in contact uniformly with the allyl isothiocyanate and achieve bacteriostatic or germicidal treatment sufficiently.

According to the allyl isothiocyanate spray of this invention, no equipment for vaporizing allyl isothiocyanate is necessary. When the present allyl isothiocyanate spray is used in an actual application, it can be utilized conveniently for various purposes only by carrying the pressure vessel to the desired spots. Besides, safety of the spray can be secured, since the combustible allyl isothiocyanate is jetted together with inert carbon dioxide gas.

According to the present spray, a gaseous composition containing 0.1 to 10% by weight of allyl isothiocyanate can sufficiently exhibit bacteriostatic or germicidal effect with no secondary affect such as of scent or irritating odor. An allyl isothiocyanate content of less than 0.1% by weight will sometimes bring about insufficient bacteriostatic or germicidal effect; whereas that of more than 10% by weight is liable to cause secondary affect such as of strong irritating odor and the like.

Now that it was identified according to this invention that even a very small amount of allyl isothiocyanate can exhibit bacteriostatic or germicidal effect, a minimum necessary amount of allyl isothiocyanate may be dissolved in liquefied carbon dioxide gas to obviate such strong irritating odor in practical uses. If even such reduced level of irritating odor is still felt offensive, a deodorizer may as necessary be used at the same time or separately.

As allyl isothiocyanate, use may be made of any natural or synthetic allyl isothiocyanate. Allyl isothiocyanate is not restricted solely to a single solid preparation consisting of 100% of allyl isothiocyanate, and a mixture oil containing allyl isothiocyanate, an extract of mustard or Japanese horseradish (usually contains above 90% of allyl isothiocyanate), or a crude product may be used.

DETAILED DESCRIPTION OF PREFERRED EMBODIMENTS

Figure 1:
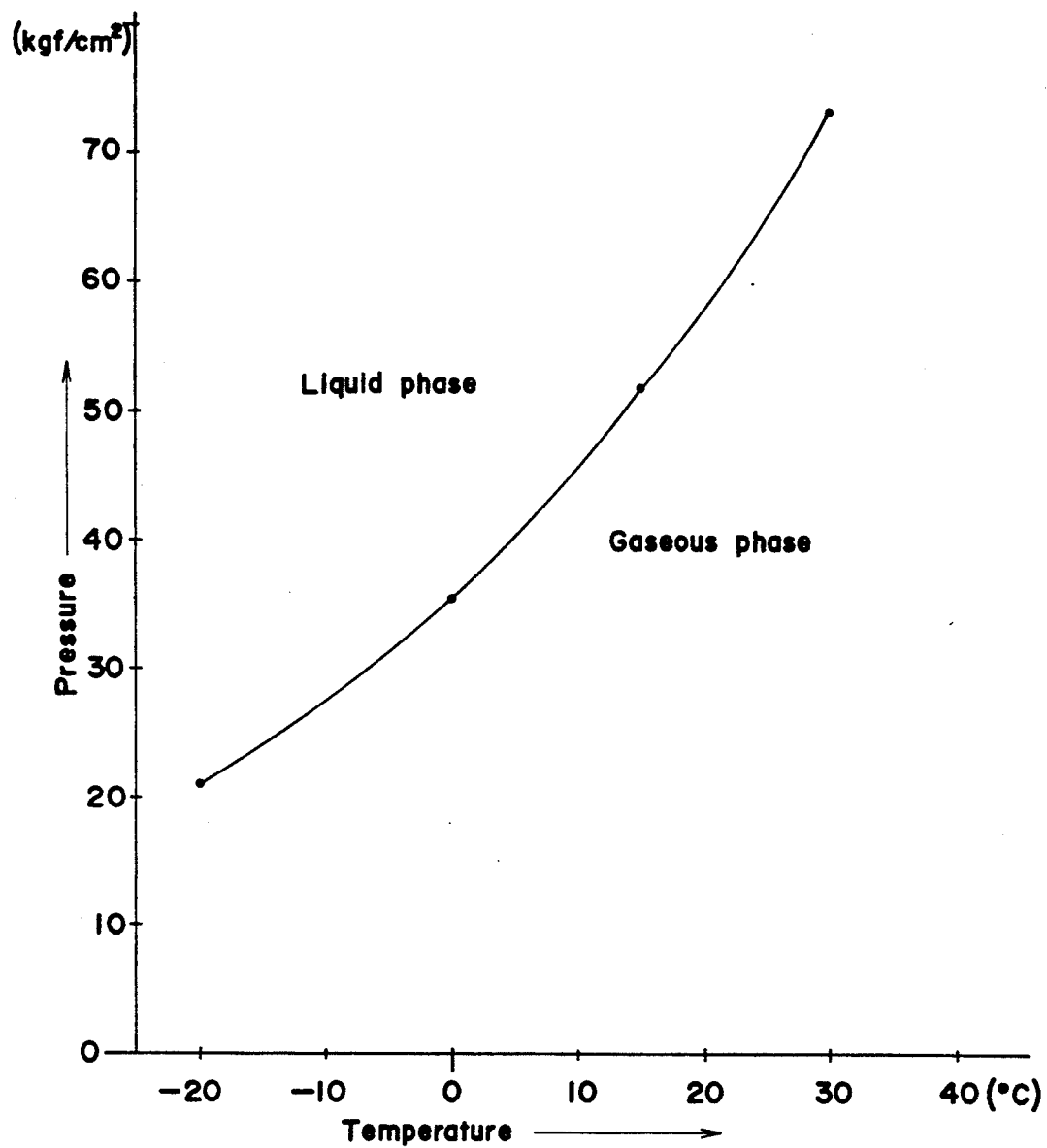
FIG. 1 is a graph showing a relationship between the temperature and pressure generally necessary for liquefied carbon dioxide gas to retain liquid phase.

Next, a preparation process and a preparation example of the spray according to this invention as well as Test Examples when the sprays thus prepared were used for bacteriostatic or germicidal treatment will be described below. It should be appreciated, however, that the present invention is not limited only to them.

A process for preparing the allyl isothiocyanate spray will be described below.

To a 3 l volume pressure vessel is charged 0.1 to 10% by weight of allyl mustard oil based on the liquefied carbon dioxide gas to be charged later. The amount of the allyl mustard oil can easily be calculated from the weight of the entire composition after liquefied carbon dioxide gas is charged with pressure to the vessel.

Subsequently, liquefied carbon dioxide gas is charged to the pressure vessel having already charged therein an allyl mustard oil in such an amount that the content of the allyl mustard oil may be 0.1 to 10% by weight. The relationship between the temperature and the pressure generally required for the liquefied carbon dioxide gas so as to maintain liquid phase is as shown in FIG. 1. Namely, in order that liquefied carbon dioxide gas can maintain liquid phase, a pressure of about 20 kgf/cm$^2$ or more at a temperature of $-20°$ C., about 35 kgf/cm$^2$ or more at a temperature of $0°$ C., about 52 kgf/cm$^2$ or more at a temperature of $15°$ C. or about 73 kgf/cm$^2$ or more at a temperature of $30°$ C. is required. When liquefied carbon dioxide gas is charged into a pressure vessel with a pressure not lower than the prescribed level at the corresponding temperature, a temperature change will occur upon completion of charging, causing a pressure change conforming to the curve shown in FIG. 1, and thus the liquefied carbon dioxide gas can maintain the liquid phase.

Since liquefied carbon dioxide gas is usually stored in a heat-insulated container under a pressure of about 20 kgf/cm$^2$ at a temperature of about $-20°$ C., a predetermined amount of liquefied carbon dioxide gas is charged therefrom maintaining this temperature into the pressure vessel preliminarily charged with an allyl mustard in such an amount that the content of allyl mustard oil may be 0.1 to 10% by weight. If the resulting pressure vessel is left to stand at room temperature, for example at $20°$ C., the pressure will be elevated to about 60 kgf/cm$^2$; whereas if the pressure vessel is left to stand at about $28°$ C., the pressure will be elevated to about 70 kgf/cm$^2$, providing a plenum fill state in the pressure vessel with the liquefied carbon dioxide gas while maintaining liquid phase.

Meanwhile, when a liquefied carbon dioxide gas stored in a heat-insulated container under a pressure of about 20 kgf/cm$^2$ at a temperature of $-20°$ C. is fed, for example, at a temperature of about $28°$ C. to a pressure vessel preliminarily charged with a predetermined amount of allyl mustard oil by means of a cryogenic gas pump, the liquefied carbon dioxide gas may be charged to a pressure of about 70 kgf/cm$^2$ where it can retain liquid phase at about $28°$ C.

An allyl isothiocyanate spray comprising 0.1 to 10% by weight of an allyl mustard oil and 99.9 to 90% by weight of liquefied carbon dioxide gas can thus be obtained.

Preparation Example of Allyl Isothiocyanate Spray

According to the process as described above, the present inventors prepared allyl mustard oil sprays by dissolving 1% by weight of an allyl mustard oil in liquefied carbon dioxide gas under a pressure of 70 kgf/cm$^2$ at a temperature of about $28°$ C. and by dissolving 3% by weight of an allyl mustard oil likewise in liquefied carbon dioxide gas under a pressure of 70 kgf/cm$^2$ at a temperature of about $28°$ C., respectively.

Next, Test Examples using these sprays will be described.

TEST EXAMPLE 1

About 1 kg of chopped vegetables was almost equally divided into nine portions and packed in nine polyethylene film bags (thickness: 20 μm). Three of them were treated externally with the spray containing 1% by weight of allyl mustard oil for about one second through the spraying means provided for the pressure vessel, and another three bags were treated with the same spray for about 10 seconds. The rest were untreated as controls.

These samples were incubated at room temperature for 24 hours to compare change in the freshness of the treated and untreated chopped vegetables. The results of observation are as shown in Table 1.

TABLE 1

| Spraying | Results of observation | |
|---|---|---|
| time | Browning | Odor development |
| Untreated | 3/3 | 3/3 |
| 1 sec | 1/3 | 0/3 |
| 10 sec | 0/3 | 0/3 |

As shown in Table 1, positive quality preservation effect was exhibited by treatment with the above sprays.

TEST EXAMPLE 2

Twenty-one packs of raw seaweed (*Undaria pinnatifida*) were divided into seven groups each group consisting of three packs. One group was untreated as a control group, and the rest of the groups were treated with the sprays containing 1% by weight and 3% by weight of allyl mustard oil under the conditions as shown in Table 2, respectively. These spraying treatments were carried out against the contents taken out of the packages and then packed in the same packages. The thus treated samples were incubated at a temperature of $10°$ C. and at a humidity of 90% for two weeks at the longest to test the following items.

1) Fungus resistance: after 1, 7 and 14 days
2) Residual smell of Japanese horseradish: immediately after treatment and after 1 day
3) General viable cell count: after 1 and 4 days The test results are as shown in Table 3.

TABLE 2

| | Ally mustard oil concentration | | | | | |
|---|---|---|---|---|---|---|
| | 1% by weight | | | 3% by weight | | |
| Condition No. | 1 | 2 | 3 | 4 | 5 | 6 |
| Spraying time (sec) | 10 | 20 | 30 | 10 | 20 | 30 |

TABLE 3

| | Test result | | | | | | |
|---|---|---|---|---|---|---|---|
| | Appearance* | | | Residual horseradish odor | | General viable cell count | |
| Treating condition | After 1 day | After 7 days | After 14 days | Immed. after | After 1 day | After 1 day | After 4 days |
| Control | − | − | + | − | − | $1.0 \times 10^6$/g | $1.9 \times 10^8$/g |
| Treated group 1 | − | − | ± | ± | − | $6.4 \times 10^3$/g | $1.1 \times 10^7$/g |
| Treated group 2 | − | − | ± | ± | − | $8.4 \times 10^2$/g | $8.5 \times 10^6$/g |
| Treated group 3 | − | − | − | ± | − | $8.5 \times 10^2$/g | $2.9 \times 10^6$/g |
| Treated group 4 | − | − | − | + | − | $8.8 \times 10^3$/g | $1.8 \times 10^7$/g |
| Treated group 5 | − | − | − | + | − | $1.5 \times 10^3$/g | $5.3 \times 10^5$/g |
| Treated group 6 | − | − | − | + | − | $9.6 \times 10^2$/g | $7.4 \times 10^4$/g |

*Appearance was evaluated according to the following criteria:
+: Molding occurred substantially over the entire surface.
±: Molding occurred at some parts.
−: No change As apparent from Table 3, in the treated groups using the above two types of sprays, not only molding was prevented but also the general viable cell count was controlled to about $1/10^2$ to $10^3$ compared with the control groups, showing a positive bacteriostatic effect. On the other hand, although the odor of Japanese horseradish was identified immediately after treatment proportional to the intensity of treatment, the odor was diminished to a undetectable degree after 1 day. This suggests that the original taste or flavor of the food may not substantially be affected.

What is claimed is:

1. A method of making an allyl isothiocyanate aerosol comprising
    dissolving 0.1 to 10% by weight of an allyl isothiocyanate in liquid carbon dioxide in a pressurized vessel to form a solution; and
    discharging the solution from the pressurized vessel whereby the liquid carbon dioxide acts as a propellant to form the allyl isothiocyanate aerosol.

2. An allyl isothiocyanate solution for use to form a bacteriostatic or germicidal aerosol comprising 0.1 to 10% by weight of allyl isothiocyanate dissolved in 99.9 to 90% by weight of liquid carbon dioxide.

3. An allyl isothiocyanate aerosol made by the process of
    dissolving 0.1 to 10% by weight of an allyl isothiocyanate in liquid carbon dioxide in a pressurized vessel to form a solution; and
    discharging the solution from the pressurized vessel, whereby the liquid carbon dioxide acts as a propellant to form the allyl isothiocyanate aerosol.

4. An aerosol spray comprising 0.1 to 10% by weight of allyl isothiocyanate dissolved in liquid carbon dioxide to form a solution wherein the solution is under sufficient pressure to be in a liquid phase.

* * * * *